United States Patent [19]
Bachmann et al.

[11] Patent Number: 5,939,466
[45] Date of Patent: *Aug. 17, 1999

[54] POLY-UNSATURATED CARBOHYDRATE DERIVATIVES, POLYMERS THEREOF AND THEIR USE

[75] Inventors: Frank Bachmann, Freiburg, Germany; Dieter Lohmann, Münchenstein, Switzerland; Peter Chabrecek, Clayton, Australia

[73] Assignee: Novartis AG, Basel, Switzerland

[ * ] Notice: This patent is subject to a terminal disclaimer.

[21] Appl. No.: 08/817,044

[22] PCT Filed: Oct. 16, 1995

[86] PCT No.: PCT/EP95/04052

§ 371 Date: Apr. 4, 1997

§ 102(e) Date: Apr. 4, 1997

[87] PCT Pub. No.: WO96/13511

PCT Pub. Date: May 9, 1996

[30] Foreign Application Priority Data

Oct. 27, 1994 [EP] European Pat. Off. ............... 94810620

[51] Int. Cl.$^6$ .................... C07H 15/02; C07H 265/04
[52] U.S. Cl. ................ 523/106; 264/11; 526/238.23; 536/17.2; 536/17.9; 536/103; 536/123.1; 536/123.13; 560/159; 560/222; 564/59
[58] Field of Search ............... 523/106; 264/11; 526/238.23; 536/17.2, 17.9, 103, 123.1, 123.13; 560/159, 222; 564/59

[56] References Cited

U.S. PATENT DOCUMENTS

| | | | |
|---|---|---|---|
| 4,451,629 | 5/1984 | Tanaka et al. | 526/238.23 |
| 5,690,953 | 11/1997 | Molock et al. | 523/106 |

FOREIGN PATENT DOCUMENTS

| | | |
|---|---|---|
| 0331633A2 | 2/1989 | European Pat. Off. . |
| 0383023 | 1/1990 | European Pat. Off. . |
| 92016959 | 9/1992 | European Pat. Off. . |
| 0668294A1 | 2/1994 | European Pat. Off. . |
| 59-193846 | 2/1984 | Japan . |

*Primary Examiner*—Peter A. Szekely
*Attorney, Agent, or Firm*—Michael U. Lee

[57] ABSTRACT

The present invention relates to polymerizable derivatives of carbohydrates comprising a carbohydrate radical and more than one radically polymerizable hydrocarbon group which is linked optionally via a spacer to the carbohydrate radical, to homopolymers, copolymers, block copolymers, graft copolymers and polymeric networks thereof, to capsules, fibers, films and coatings having water-binding and biocompatible properties, and to molded articles, for example contact lenses or biomedicinal articles, comprising the mentioned polymers, as well as to processes for the preparation of the mentioned polymers and articles.

27 Claims, No Drawings

POLY-UNSATURATED CARBOHYDRATE DERIVATIVES, POLYMERS THEREOF AND THEIR USE

The present invention relates to polymerisable derivatives of carbohydrates comprising a carbohydrate radical and more than one radically polymerisable hydrocarbon group which is linked optionally via a spacer to the carbohydrate radical, to copolymers, branched polymers, block copolymers, graft copolymers and polymeric networks thereof, to capsules, fibres, films and coatings having water-binding and biocompatible properties, and to moulded articles, for example contact lenses or biomedicinal articles, comprising the mentioned polymers, as well as to processes for the preparation of the mentioned polymers and articles.

Moulded articles, for example contact lenses, or coatings for biomedicinal articles having water-binding and biocompatible properties place high demands on the material used. The search for suitable starting materials for the preparation of such products, which are mentioned by way of example, is therefore of great importance.

JP 4 316 594 describes, for example, a methacrylate that is linked to a carbohydrate in which from 50 to 100% of the hydrogen atoms of the amino or hydroxy groups preferably have been esterified by aromatic hydrocarbons. Those compounds can be polymerised, but they are then used as a stationary phase in chromatography, especially for the separation of chiral compounds.

A carbohydrate derivative, for example isomannitol dimethacrylate, is described in Angew. Makromol. Chemie 123/124, 241 (1984) as a cross-linking agent for polymeric networks, especially to control the water content in polyhydroxyethyl methacrylate (poly-HEMA) hydrogels. Those hydrogels are used in the manufacture of contact lenses.

European Patent 331 633 describes hydrophilic monomers carrying one or more polymerisable or reactive groups that are each bonded via a divalent group to a mono- or poly-valent hydrophilic group. The number and nature of the polymerisable or reactive groups and the nature of the hydrophilic group determine the properties of a product produced therefrom. As a preferred compound there is disclosed, for example, a polyvinyl alcohol (PVA) modified by 2-isocyanatoethyl methacrylate (IEM). Although carbohydrates are mentioned as hydrophilic groups, they are not specifically disclosed. The mentioned monomers are, for example, suitable for the manufacture of contact lenses.

It has now been found that unprotected carbohydrate derivatives can be reacted with unsaturated compounds, especially isocyanates, to form polysubstituted derivatives. As a result of such a reaction, new unsaturated carbohydrate derivatives modified by at least two polymerisable ligands are isolated. The resulting poly-unsaturated carbohydrate derivatives are especially suitable for use as cross-linking agents in the synthesis of polymers. They can also be converted into polymers having a high carbohydrate content. Such polymers are to be understood as being especially copolymers and block copolymers and also graft copolymers, especially branched and crosslinked polymerisates, which can be obtained, for example, by radical polymerisation or photopolymerisation.

Accordingly, the present invention relates to a compound of formula (I)

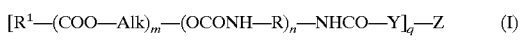

wherein
R$^1$ is a radically polymerisable hydrocarbon group;
m and n are each independently of the other 0 or 1;
q is an integer from 2 up to the full valency of Z;
Alk is an alkylene having up to 10 carbon atoms;
R is a diradical, having up to 20 carbon atoms, of an organic diisocyanate;
each Y is independently —O— or —NH—;
Z is a radical, less q hydroxy and optionally amino groups, of a saccharide selected from a mono-, di- or tri-saccharide, an oligosaccharide, a cyclodextrin (CD) and an anhydrosaccharide, or of a conventional derivative of the mentioned saccharides;
with the proviso that per saccharide unit Z, Y is —NH— a maximum of twice, and the remaining Y are —O—.

R$^1$ is, for example, alkenyl, vinylphenyl or vinylbenzyl in the form of a radically polymerisable group having preferably from 2 to 12 carbon atoms. Examples of alkenyl are vinyl, allyl, 1-propen-2-yl, 1-buten-2- or -3- or -4-yl, 2-buten-3-yl, and the isomers of pentenyl, hexenyl, octenyl, decenyl, undecenyl and dodecenyl. R$^1$ contains preferably from 2 to 12 and more especially from 2 to 8 carbon atoms. In a preferred meaning, R$^1$ within the scope of this invention is alkenyl having from 2 to 4 carbon atoms.

The diradical R is, for example, lower alkylene, arylene, a saturated bivalent cycloaliphatic group having from 6 to 10 carbon atoms, alkylenearylene, arylenealkylene or arylenealkylenearylene.

Arylene is preferably phenylene or naphthylene that is unsubstituted or substituted by lower alkyl or by lower alkoxy, especially 1,3-phenylene, 1,4-phenylene or methyl-1,4-phenylene; or 1,5-naphthylene or 1,8-naphthylene.

A saturated bivalent cycloaliphatic group is preferably cyclohexylene or cyclohexylene-lower alkylene, for example cyclohexylenemethylene, that is unsubstituted or substituted by one or more lower alkyl groups, for example methyl groups, for example trimethylcyclohexylenemethylene, for example the bivalent isophorone radical.

Within the scope of this invention, unless defined otherwise the term "lower" used in connection with radicals and compounds denotes especially radicals or compounds having up to 8 carbon atoms, preferably up to 6 carbon atoms.

Lower alkyl has especially up to 8 carbon atoms, preferably up to 6 carbon atoms, and is, for example, methyl, ethyl, propyl, butyl, tert-butyl, pentyl, hexyl or isohexyl.

Alkylene has up to 10 carbon atoms and may be straight-chained or branched. Suitable examples include decylene, octylene, hexylene, pentylene, butylene, propylene, ethylene, methylene, 2-propylene, 2-butylene and 3-pentylene. Alkylene is preferably lower alkylene.

Lower alkylene denotes alkylene having up to 8, and especially up to 6, carbon atoms. An especially preferred meaning of lower alkylene is methylene or ethylene.

The arylene component of alkylenearylene or arylenealkylene is preferably phenylene that is unsubstituted or substituted by lower alkyl or by lower alkoxy; the alkylene component thereof is preferably lower alkylene, such as methylene or ethylene, especially methylene. Accordingly, such radicals are preferably phenylenemethylene or methylenephenylene.

Lower alkoxy has especially up to 8 carbon atoms, preferably up to 6 carbon atoms, and is, for example, methoxy, ethoxy, propoxy, butoxy, tert-butoxy or hexyloxy.

Arylenealkylenearylene is preferably phenylene-lower alkylene-phenylene having up to 8, and especially having up to 6, carbon atoms in the alkylene component, for example phenyleneethylenephenylene.

In accordance with the definition, the degree of substition q of a carbohydrate derivative within the scope of this invention is from 2 up to its full valency. The full valency of a carbohydrate derivative is to be understood as being the total number of the free hydroxy and optionally the free amino groups. q is preferably from 2 to 5, especially from 2 to 4 and more especially 2 or 3.

Within the scope of the present invention, a monosaccharide is to be understood as being an aldopentose, aldohexose, aldotetrose, ketopentose or ketohexose. The mentioned compounds may also be in the form of lactones.

Examples of an aldopentose are D-ribose, D-arabinose, D-xylose or D-lyose; examples of an aldohexose are D-allose, D-altrose, D-glucose, D-mannose, D-gulose, D-idose, D-galactose, D-talose, L-fucose or L-rhamnose; examples of a ketopentose are D-ribulose or D-xylulose; examples of a tetrose are D-erythrose or threose; and examples of a ketohexose are D-psicose, D-fructose, D-sorbose or D-tagatose.

Examples of a disaccharide are trehalose, maltose, isomaltose, cellobiose, gentiobiose, saccharose, lactose, chitobiose, N,N-diacetylchitobiose, palatinose or sucrose.

As trisaccharides there may be mentioned by way of example raffinose, panose or maltotriose.

As oligosaccharides there may be mentioned by way of example maltotetraose, maltohexaose or chitoheptaose.

Cyclodextrins contain from 6 to 8 identical units of α-1,4-glucose. Some examples of cyclodextrins are α-, β- and γ-cyclodextrin, hydroxypropylcyclodextrin and branched cyclodextrins.

An anhydrosaccharide is to be understood as being a saccharide formed by the removal of one or more molecules of water from a corresponding mono-, di-, tri- or oligo-saccharide.

Examples of anhydrosaccharides are 1,6-anhydrosaccharides, for example levoglucosan (1,6-anhydro-β-D-glucopyranoside). Other possible variants are the isomeric 1,2-, 1,3-, 1,4- and 1,5-anhydrosaccharides. Examples of 1,4-anhydrosaccharides are anhydroerythritol and threitol.

A preferred anhydrosaccharide is, for example, levoglucosan (1,6-anhydro-β-D-glucopyranoside).

Examples of dianhydrosaccharides are 1,4:3,6-dianhydro-D-sorbitol, 1,4:3,6-dianhydro-D-mannitol or 1,4:3,6-dianhydro-L-iditol.

A preferred dianhydromonosaccharide is, for example, 1,4:3,6-dianhydro-D-sorbitol.

A conventional derivative of a saccharide is to be understood within the scope of the present invention as being, for example, a lactone, an amino sugar (aminodeoxysaccharide) or a lower alkyl glycoside.

Within the scope of the present invention, Z is preferably a monosaccharide, disaccharide, anhydrosaccharide or a cyclodextrin. Z is more especially a monosaccharide, a disaccharide or an anhydrosaccharide, especially a disaccharide or an anhydrosaccharide.

The present invention relates preferably to a compound of formula (I) wherein per saccharide unit Z, Y is —NH— a maximum of once.

The present invention relates preferably to a compound of formula (I) wherein Y is —O—.

The present invention relates preferably to a compound of formula (I) wherein m=1 and n=0.

The present invention relates preferably to a compound of formula (I) wherein m and n are each 0.

The present invention relates preferably to a compound of formula (I) wherein the radically polymerisable group $R^1$ is other than vinyl when m=0 and n=1.

In a preferred form of formula (I), $R^1$ is alkenyl having from 2 to 12, especially from 2 to 8 and more especially from 2 to 4, carbon atoms.

In a compound of formula (I), Alk is preferably a lower alkylene having up to 8, especially up to 6 and more especially up to 2, carbon atoms.

The present invention relates preferably also to a compound of formula (I) wherein the diradical R is lower alkylene, arylene, a saturated bivalent cycloaliphatic group having from 6 to 10 carbon atoms, alkylenearylene, arylenealkylene or arylenealkylenearylene.

The present invention relates preferably also to a compound of formula (I) wherein the diradical R is lower alkylene.

The present invention relates preferably to a compound of formula (I) wherein the radical Z is derived from a monosaccharide selected especially from an aldohexose and a ketohexose and more especially from a 1-lower alkyl glucoside.

The present invention relates preferably also to a compound of formula (I) wherein the radical Z is derived from a disaccharide selected from a trehalose, maltose, isomaltose, cellobiose, gentiobiose, saccharose and lactose.

Preference is given also to a compound of formula (I) wherein the radical Z is derived from a disaccharide selected from an α,α-, α,β- and β,β-trehalose and especially from a α,α-trehalose.

Preference is given also to a compound of formula (I) wherein the radical Z is derived from a cyclodextrin selected from an α-, β- and γ-cyclodextrin, especially from an α- and β-cyclodextrin and more especially from an α-cyclodextrin.

Preference is given also to a compound of formula (I) wherein the radical Z is derived from an anhydrosaccharide.

Strong preference is given to a compound of formula (I) wherein $R^1$ is alkenyl having from 2 to 8 carbon atoms; m is 1 and n is 0; q is from 2 to 4; Alk is a lower alkylene having up to 4 carbon atoms; Y is —O—; and the radical Z is derived from a saccharide which is a 1-alkyl glycoside of an aldohexose, or a trehalose, a cyclodextrin or an anhydrosaccharide.

Special preference is given also to a compound of formula (I) wherein $R^1$ is alkenyl having from 2 to 8 carbon atoms; m and n are 0; Y is —O— and —NH—; and the radical Z is derived from a saccharide which is a 1-alkyl glycoside of an aldohexose, or a trehalose, a cyclodextrin or an anhydrosaccharide.

Strong preference is given to a compound of formula (I) wherein $R^1$ is alkenyl having from 2 to 4 carbon atoms; m=0 and n=0; and Alk is lower alkylene having up to 4 carbon atoms.

Very strong preference is given to a compound of formula (I) wherein $R^1$ is alkenyl having from 2 to 4 carbon atoms; m=1 and n=0; Y is —O—; and Alk is lower alkylene having up to 4 carbon atoms.

Strong preference is given also to a compound of formula (I) wherein q is 2 and Z is a radical, less two hydroxy groups, of an anhydrosaccharide.

The preparation of a claimed compound of formula (I) generally results in the formation of a monomer mixture wherein in addition to monosubstituted saccharide, which is typically formed in very small amounts, there is also formed bis-, tris-, tetrakis-, pentakis- and in some cases also higher-substituted saccharide. Such a monomer mixture can be separated and the individual monomers according to formula (I) wherein q is at least 2 can be used, for example, in pure form especially as cross-linking agents. Such a mixture can, however, also be used advantageously directly in a polymerisation.

The present invention relates also to a polymer comprising the polymerisation product of a monomer mixture formed in the preparation of a monomer as defined in formula (I) and optionally of at least one other vinylic comonomer (a) that is different therefrom.

The present invention relates also to a process for the preparation of a compound of formula (I) as defined in claim 1, which process comprises reacting a saccharide of formula (II)

$$[Z]\!-\!X_q \qquad\qquad (II),$$

wherein Z is as defined in claim 1 and X is a reactive group, preferably with q equivalents of a derivative of formula (III)

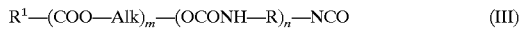

$$R^1\!-\!(COO\!-\!Alk)_m\!-\!(OCONH\!-\!R)_n\!-\!NCO \qquad (III)$$

wherein the variables are as defined in the main claim. If the preparation of a compound of formula (I) results in mixtures, those mixtures may, if desired, be separated using conventional methods.

The reactive group X is typically a hydroxy or amino group which yields a urethane or a urea with an isocyanate of formula (III).

When the reactive group X is a hydroxy or amino group, that group may be in the form of a primary or secondary group. If a saccharide of formula (II) is reacted with a derivative of formula (III), the following applies to the reaction sequence in the starting material: amino reacts much more quickly than hydroxy, and primary groups react more quickly than secondary groups. In accordance with that reactivity, the various positions in a starting material of formula (II) are also occupied in that sequence.

The compounds according to the invention can be prepared in the presence or absence of a solvent. Advantageously, a solvent is used that is substantially inert, that is to say that does not take part in the reaction. Suitable examples of such solvents are ethers, such as tetrahydrofuran (THF), diethyl ether, diethylene glycol monomethyl ether or dioxane, halogenated hydrocarbons, such as chloroform or methylene chloride, dipolar aprotic solvents, such as acetonitrile, acetone, dimethylformamide (DMF), hexamethylphosphoramide (HMPA), N-methylpyrrolidone (NMP) or dimethyl sulfoxide (DMSO), and also pyridine or N-methylmorpholine.

In the preparation of the compounds according to the invention, the reactants are advantageously employed in stoichiometric amounts. The reaction temperature may be, for example, from −30° to 150° C. The range from 0° to 60° C. and especially from 0° to 40° C. is a preferred temperature range. The reaction times are in the range of approximately from 15 minutes to 7 days, preferably approximately 12 hours. If necessary, the reaction is carried out under argon or nitrogen as protecting gas.

The present invention relates also to a polymer comprising a polymerisation product of at least one compound of formula (I) according to the definition given above and optionally of at least one other vinylic comonomer (a) that is different therefrom.

The preferred composition of a polymer according to the invention is as follows: the proportion by weight, based on the total polymer, of a compound of formula (I) is in the range of from 90 to 0.5%, especially in the range of from 60 to 1% and preferably in the range of from 40 to 2%.

A comonomer (a) that is present in a polymer according to the invention may be hydrophilic or hydrophobic, or a mixture of the two. Suitable comonomers include especially those which are customarily used in the manufacture of contact lenses and biomedicinal materials.

A hydrophobic comonomer (a) is to be understood as being a monomer that, as a homopolymer, typically yields a polymer that is insoluble in water and can absorb less than 10% by weight water.

Analogously, a hydrophilic comonomer (a) is to be understood as being a monomer that, as a homopolymer, typically yields a polymer that is soluble in water or can absorb at least 10% by weight water.

Suitable hydrophobic comonomers (a) include the following, this list not being exhaustive: $C_1$–$C_{18}$alkyl and $C_3$–$C_{18}$cycloalkyl acrylates and methacrylates, $C_3$–$C_{18}$alkyl-acrylamides and -methacrylamides, acrylonitrile, methacrylonitrile, vinyl-$C_1$–$C_{18}$alkanoates, $C_2$–$C_{18}$alkenes, $C_2$–$C_{18}$haloalkenes, styrene, lower alkylstyrenes, lower alkyl vinyl ethers, $C_2$–$C_{10}$perfluoroalkyl acrylates and methacrylates or correspondingly partially fluorinated acrylates and methacrylates, $C_3$–$C_{12}$perfluoroalkyl-ethyl-thiocarbonylaminoethyl acrylates and methacrylates, acryloxy- and methacryloxy-alkylsiloxanes, N-vinylcarbazole, $C_1$–$C_{12}$alkyl esters of maleic acid, fumaric acid, itaconic acid, mesaconic acid and the like. Preference is given to, for example, acrylonitrile, $C_1$–$C_4$alkyl esters of vinylically unsaturated carboxylic acids having from 3 to 5 carbon atoms, or vinyl esters of carboxylic acids having up to 5 carbon atoms.

Examples of suitable hydrophobic comonomers (a) include methyl acrylate, ethyl acrylate, propyl acrylate, isopropyl acrylate, cyclohexyl acrylate, 2-ethylhexyl acrylate, methyl methacrylate, ethyl methacrylate, propyl methacrylate, butyl acrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyltoluene, vinyl ethyl ether, perfluorohexylethylthiocarbonylaminoethyl methacrylate, isobornyl methacrylate, trifluoroethyl methacrylate, hexafluoroisopropyl methacrylate, hexafluorobutyl methacrylate, tris-trimethylsilyloxy-silyl-propyl methacrylate, 3-methacryloxypropylpentamethyldisiloxane and bis(methacryloxypropyl)tetramethyldisiloxane.

Preferred examples of hydrophobic comonomers (a) are isobutyl and n-butyl acrylate, 2-ethylhexyl acrylate, cyclohexyl acrylate, tris-trimethylsilyloxy-silyl-propyl methacrylate, methyl methacrylate and acrylonitrile.

Suitable hydrophilic comonomers (a) include the following, this list not being exhaustive: hydroxy-substituted lower alkyl acrylates and methacrylates, acrylamide, methacrylamide, lower alkyl-acrylamides and -methacrylamides, ethoxylated acrylates and methacrylates, hydroxy-substituted lower alkyl-acrylamides and -methacrylamides, hydroxy-substituted lower alkyl vinyl ethers, sodium vinylsulfonate, sodium styrenesulfonate, 2-acrylamido-2-methylpropanesulfonic acid, N-vinylpyrrole, N-vinyl-2-pyrrolidone, 2- and 4-vinylpyridine, vinylically unsaturated carboxylic acids having a total of from 3 to 5 carbon atoms, amino-lower alkyl- (the term "amino" also including quaternary ammonium), mono-lower alkylamino-lower alkyl- and di-lower alkylamino-lower alkyl-acrylates and -methacrylates, allyl alcohol and the like. Preference is given to, for example, N-vinyl-2-pyrrolidone, acrylamide, methacrylamide, hydroxy-substituted lower alkyl acrylates and methacrylates, hydroxy-substituted lower alkyl-acrylamides and -methacrylamides, and vinylically unsaturated carboxylic acids having a total of from 3 to 5 carbon atoms.

Examples of suitable hydrophilic comonomers (a) include hydroxyethyl methacrylate, hydroxyethyl acrylate, hydroxypropyl acrylate, ammonium ethyl methacrylate hydrochloride, N,N-dimethylaminoethyl acrylate and methacrylate, acrylamide, methacrylamide, N,N-dimethylacrylamide, allyl alcohol, vinylpyridine, glycerol methacrylate, N-(1,1-dimethyl-3-oxobutyl)acrylamide, N-vinyl-2-pyrrolidone, acrylic acid, methacrylic acid and the like.

Preferred hydrophilic comonomers (a) are 2-hydroxyethyl methacrylate, acrylamide, N,N-dimethylacrylamide, N,N-dimethylaminoethyl acrylate and methacrylate, and N-vinyl-2-pyrrolidone.

The polymers according to the invention are formed in a manner known per se from the corresponding monomers by means of a polymerisation reaction known to the person skilled in the art. Customarily, a mixture of the above-mentioned monomers, with the addition of a radical-former, is optionally heated. Such a radical-former is, for example, azobisisobutyronitrile (AIBN), potassium peroxodisulfate, dibenzoyl peroxide, hydrogen peroxide, sodium percarbonate etc. If, for example, the said compounds are heated, then there are formed, with homolysis, radicals which may then, for example, induce polymerisation.

Especially preferred are redox polymerisation initiators, for example the mixtures ammonium peroxodisulfate/sodium disulfite or $Fe^{2+}$ (e.g. $FeSO_4$)/hydrogen peroxide.

Polymerisation may be carried out in the presence or absence of a solvent. In principle, there are suitable as solvent all solvents that dissolve the monomers used and that do not to any significant extent result in transfer reactions or chain-terminating reactions during the radical chain reaction. Suitable solvents are, for example, water, alcohols, such as lower alkanols, for example ethanol or methanol; also carboxylic acid amides, such as dimethylformamide; dipolar aprotic solvents, such as dimethyl sulfoxide; hydrophobic solvents, such as alkanes, for example n-hexane, cyclohexane or paraffins; aromatic hydrocarbons, for example toluene, xylene or pyridine; and also mixtures of suitable solvents, for example mixtures of water with an alcohol, for example a water/ethanol or water/methanol mixture.

Polymerisation can also be carried out heterogeneously. For heterogeneous polymerisations it is preferable to use a solvent in which the monomers used have poor solubility. The polymerisation is effected in emulsion or suspension, which produces polymers in the form of micropearls. The latter can be used, for example, as carriers for drug delivery systems.

In the case of photopolymerisation it is appropriate to add a photoinitiator which can initiate radical polymerisation. Examples thereof are known to the person skilled in the art; there may be mentioned specifically as suitable photoinitiators benzoin methyl ether, 1-hydroxycyclohexyl phenyl ketone, and Darocur and Irgacur types, preferably Darocur 1173® and Irgacur 2959®, and also derivatives of Irgacur 2959® that have been esterified by methacrylic acid. The polymerisation can then be initiated by means of actinic radiation, for example UV light of a suitable wavelength.

The monomers and monomer mixtures according to the invention can be processed in a manner known per se to form moulded articles, especially contact lenses, for example by carrying out the photopolymerisation of the monomers or monomer mixtures in a suitable contact lens mould. The invention therefore relates also to moulded articles that consist essentially of polymers according to the invention. Further examples of moulded articles according to the invention, in addition to contact lenses, are biomedicinal articles and, especially, ophthalmic moulded articles, for example artificial corneas, intraocular lenses and eye dressings, moulded articles for use in surgery, such as heart valves, artificial arteries or the like, and also films, fibres or membranes, for example membranes for controlling diffusion, photostructurable foils for information storage, or photoresist materials, for example membranes or moulded articles for etching resist or screen printing resist.

A specific embodiment of the invention relates to contact lenses that consist essentially or completely of a polymer according to the invention. Such contact lenses exhibit a range of unusual and highly advantageous properties. Of those properties, mention may be made of, for example, their excellent tolerability by the human cornea and by lachrymal fluid, which is based on a balance of water content, oxygen permeability and mechanical and adsorptive properties. Moreover, the contact lenses according to the invention exhibit high dimensional stability. A particular property of the polymers according to the invention is their high water retention ability which in the case of contact lenses results in a high degree of stability of the lachrymal film on the lens.

All the above-mentioned advantages naturally apply not only to contact lenses but also to other moulded articles according to the invention.

A specific application of the polymers according to the invention is in delivery systems for biologically active ingredients, for example pharmaceutically active ingredients (drug delivery systems and cosmetics). The polymers according to the invention have a gel structure in which organic compounds, especially pharmaceutically active organic compounds, may be incorporated, if desired. If such polymers are administered locally, for example, then the pharmaceutically active ingredients exhibit their action firstly by slow and continuous release, that is to say, for example, in a diffusion-controlled manner, and secondly in a locally restricted manner, since they are bonded to a substrate (carrier).

The present invention relates also to the use of a compound of formula (I) according to the invention in the coating of a base material, for example glass, ceramics or metal, with a hydrophilic film and preferably in the coating of polymer substrates, for example products for ophthalmic use, such as contact lenses, intraocular lenses or eye dressings, and products for use in medicine.

Polymer substrates are therefore to be understood as being especially substrates made from materials that are typically used for ophthalmological lenses, especially contact lenses. Suitable polymer substrates are, for example, RGP (rigid gas permeable) lenses, e.g. Nefocon A (Ocusil), Pasifocon A (Paraperm-02), Telefocon B (SGP-II), Silafocon A (Polycon-2), Fluorsilfocon (Fluorex-400), Paflufocon A (Fluoroperm-30) or Silafocon B (Polycon-HDK); also suitable are amorphous Teflon substrates or contact lenses thereof, for example those of Teflon AF 1600 or Teflon AF 2400, the former being a copolymer of 63–73 mol % perfluoro-2,2-dimethyl-1,3-dioxole and 37–27 mol % tetrafluoroethylene, and the latter being a copolymer of 80–90 mol % perfluoro-2,2-dimethyl-1,3-dioxole and 20–10 mol % tetrafluoroethylene. Polymer substrates comprising polysiloxanes are especially suitable.

The coating of such a base material is generally carried out by means of a method known to the person skilled in the art. A compound of formula (I) according to the invention is bonded, for example, covalently by means of reactive groups to the surface of an article. If the material to be coated does not have any suitable reactive groups on its surface, then it is first treated, for example, with a plasma. Suitable reactive groups are thus incorporated into the surface of the base material. Those groups can then be derivatised, for example, with a difunctional radical which is itself able to enter into a covalent bond with a compound of formula (I) according to the invention.

Examples of suitable reactive groups are hydroxy, amino, carboxy, carbonyl, sulfonyl, sulfonyl chloride and halogens, such as bromine or iodine. Preferred reactive groups are hydroxy and amino. The method of applying reactive groups such as hydroxy or amino to the surface of an article via plasma surface treatment is described comprehensively in, for example, PCT Application WO 89/00220 (Griesser et al.).

A difunctional radical is distinguished, for example, by the fact that one functional group can form covalent bonds with the, for example, hydroxy or amino groups of the surface of the article and the other can form covalent bonds with the, for example, hydroxy groups of the compounds of formula (I). The functional groups of the difunctional radical are preferably isocyanates and the radical is selected from lower alkylene, arylene, a saturated bivalent cycloaliphatic group having from 6 to 10 carbon atoms, alkylenearylene, arylenealkylene and arylenealkylenearylene.

A further method of grafting monomers of formula (I) according to the invention onto the surface of an article comprises essentially bonding a photoreactive group to a monomer of formula (I) according to the invention or to a polymer prepared therefrom, which photoreactive group, when irradiated with UV light of a suitable wavelength, then couples to a surface pretreated with, for example, plasma oxygen. This method is described comprehensively in U.S. Pat. No. 5,002,582 or by R. L. W. Smithson et al., Colloids and Surfaces B: Biointerfaces, 1, 349–355 (1993).

A third method of applying monomers of formula (I) according to the invention to the surface of an article comprises first bonding a reactive photoinitiator to the surface of the article and then grafting on monomers of formula (I) by means of photograft polymerisation. Specific graft polymer layers having a so-called brush structure are formed, which may also be crosslinked or branched.

A coating (or film) applied by one of the methods described above typically has a layer thickness of approximately from 500 to 1500 nanometers. The layer thickness can be determined, for example, by force field microscopy.

The Examples given below serve to illustrate the present invention further, but they are not intended to limit the scope thereof in any way. Unless otherwise indicated, temperatures are given in degrees Celsius.

EXAMPLE 1

Bis- and tris-O-[2(methacryloyloxy)ethyl-carbamoyl]-methyl-α-D-glucopyranoside 2.0 g (10.3 mmol) of methyl-α-D-glucopyranoside are dissolved in 20 ml of pyridine at 0° C. One molar equivalent of 2-isocyanatoethyl methacrylate (IEM) is then added to that solution. After 6 hours a further equivalent of 2-isocyanatoethyl methacrylate is added and the mixture is stirred overnight. After 24 hours a third equivalent of 2-isocyanatoethyl methacrylate is added. After 36 hours the reaction solution is diluted with 20 ml of toluene and then concentrated. The residue is subjected to chromatographic separation on 500 g of silica gel. The eluants are: ethyl acetate (2000 ml), ethyl acetate/acetonitrile 9:1 (2000 ml), ethyl acetate/acetonitrile 1:1 (1000 ml) and methanol (1000 ml). The title compounds are obtained in the form of colourless powders.

bisacrylate: MS(FAB): 505(M+H)$^+$ R$_f$ value: 0.69 (CH$_3$CN/H$_2$O 8:2) trisacrylate: MS(FAB): 660(M+H)$^+$, 505 (diacrylate) R$_f$ value: 0.81 (ethyl acetate/methanol 8:2)

EXAMPLE 2

Bis-O-[2(methacryloyloxy)ethyl-carbamoyl]-gluconic acid γ-lactone 8.8 g (56.2 mmol) of IEM are slowly added dropwise to 5.0 g (28.1 mmol) of D(+)-gluconic acid δ-lactone in 50 ml of pyridine. The mixture is then stirred at room temperature for 2 days and then worked up as in Example 1. Purification by chromatography (ethyl acetate/methanol 8:2) yields the title compound.

MS(FAB): 489(M+H)$^+$

EXAMPLE 3

Bis- and tris-O-[2(methacryloyloxy)ethyl-carbamoyl]-α,α-trehalose 40 g (0.106 mol) of α,α-trehalose are dissolved in 400 ml of pyridine and, with stirring at room temperature, 36.3 g (0.234 mol, 2.2 equivalents) of 2-isocyanatoethyl methacrylate are slowly added dropwise thereto. The mixture is stirred overnight to complete the reaction. 300 ml of toluene are then added to the reaction solution, a white solid being precipitated. Filtration is carried out and the residue is washed with a small amount of toluene. The mother liquor is concentrated and then purified by chromatography on 1 kg of silica gel. Elution is carried out first with 2 liters of acetonitrile, then with 1.3 liters of acetonitrile/water 9:1 and finally with 2 liters of acetonitrile/water 1:1.

bisacrylate: MS(FAB): 653(M+H)$^+$ R$_f$ value: 0.75 (CH$_3$CN/H$_2$O 8:2) trisacrylate: MS(FAB): 808(M+H)$^+$

EXAMPLE 4

Bis-O-[2(methacryloyloxy)ethyl-carbamoyl]-β,β-trehalose

In a flask under argon, 1.9 g (0.292 mmol) of β,β-trehalose are dissolved in 19 ml of dry pyridine. 861 μl (5.55 mmol) of IEM are slowly added dropwise to that solution at room temperature. A marked conversion can already be detected after one hour. The reaction mixture is stirred for a further 6 hours and then worked up. The residue is purified by chromatography (300 g of silica gel, acetonitrile/water 9:1).

R$_f$ value: 0.72 (CH$_3$CN/H$_2$O 8:2). MS(FAB): 653(M+H)$^+$

EXAMPLE 5

Bis- and tris-O-[2(methacryloyloxy)ethyl-carbamoyl]-α,β-maltose

Analogously to Example 3, 10 g (0.027 mol) of maltose in pyridine are reacted with 2 equivalents of IEM. Working up and purification yield the title compounds.

bisacrylate: R$_f$ value: 0.4 (acetonitrile/water 9:1) MS(FAB): 675(M+Na)$^+$ trisacrylate: R$_f$ value: 0.5 (acetonitrile/water 9:1) MS(FAB): 830(M+Na)$^+$, 842(M+Cl)$^-$

EXAMPLE 6

Bis- and tris-O-[2(methacryloyloxy)ethyl-carbamoyl]-α,β-lactose

Analogously to Example 3, the title compounds are obtained in a similar yield; starting from lactose and IEM in pyridine.

bisacrylate: R$_f$ value: 0.51 (CH$_3$CN/H$_2$O 9:1) MS(FAB): 653(M+H)$^+$, 675(M+Na)$^+$ trisacrylate: R$_f$ value: 0.66 (CH$_3$CN/H$_2$O 9:1) MS(FAB): 830(M+H)$^+$

EXAMPLE 7

Bis-O-[2(methacryloyloxy)ethyl-carbamoyl]-1,6-anhydro-β-glucopyranose 50 g (0.308 mol) of 1,6-anhydro-β-D-glucopyranoside are dissolved in 500 ml of pyridine and at 0° C. 2 equivalents of 2-isocyanatoethyl methacrylate are added. The reaction mixture is allowed to rise to room temperature and is then stirred overnight. The reaction mixture is then concentrated and purified by chromatography (silica gel, chloroform/methanol 10:1). The title compound is obtained in the form of a colourless amorphous mass.

MS(FAB): 473(M+H)$^+$ R$_f$ value: 0.74 (ethyl acetate/acetonitrile 7:3)

EXAMPLE 8

2,5-Bis-O-[2(methacryloyloxy)ethyl-carbamoyl]-1,4:3,6-dianhydro-D-sorbitol 5 g (34 mmol) of 1,4:3,6-dianhydro-D-sorbitol are dissolved in 50 ml of pyridine and at 0° C. 2 equivalents of 2-isocyanatoethyl methacrylate are added. The mixture is allowed to rise to room temperature and is then stirred overnight. The reaction mixture is then concentrated and purified by chromatography (silica gel, chloroform/methanol 10:1). The title compound is obtained in the form of a colourless amorphous mass.

MS(FAB): 456(M)$^+$ R$_f$ value: 0.74 (chloroform/methanol 10:1)

EXAMPLE 9

2,5-Bis-O-[2(methacryloyloxy)ethyl-carbamoyl]-1,4:3,6-dianhydro-D-mannitol 5 g (34 mmol) of 1,4:3,6-dianhydro-D-mannitol are dissolved in 50 ml of pyridine and at 0° C. 2 equivalents of 2-isocyanatoethyl methacrylate are added. The reaction mixture is allowed to rise to room temperature and is then stirred overnight. The reaction mixture is then concentrated and purified by chromatography (silica gel, chloroform/ methanol 10:1). The title compound, 6.2 g (40%), is obtained in the form of a colourless amorphous mass.

MS(FAB): 457(M+H)$^+$ R$_f$ value: 0.70 (ethyl acetate)

EXAMPLE 10

Bis-O-[2(methacryloyloxy)ethyl-carbamoyl]-α,β-maltotriose 2 equivalents of 2-isocyanatoethyl methacrylate are added at room temperature to 5 g (9.9 mmol) of maltotriose in 100 ml of pyridine. After 48 hours 100 ml of toluene are added and the mixture is carefully concentrated to dryness under a high vacuum. A light-yellow oil remains behind which is purified by chromatography (400 g of silica gel, first acetonitrile/water 9:1, then acetonitrile/water 8:2 and finally acetonitrile/water 7:3). The title compound is obtained in the form of a colourless oil.

R$_f$ value: 0.21 (CH$_3$CN/H$_2$O 9:1) MS(FAB): 813(M-H)$^-$, 849(M+Cl)$^-$

EXAMPLE 11

Bis-, tris-, tetrakis-, pentakis- and hexakis-O-[2(methacryloyloxy)ethylcarbamoyl]-α-cyclodextrin 5 g (5.14 mmol) of α-cyclodextrin (α-CD) are dissolved in 50 ml of pyridine and at room temperature 2 equivalents of 2-isocyanatoethyl methacrylate are added. After 24 hours the reaction solution is concentrated and purified by chromatography on 200 g of silica gel with acetonitrile/water 9:1, then acetonitrile/water 8:2 and finally with acetonitrile/water 7:3.

bisacrylate: R$_f$ value: 0.46(CH$_3$CN/H$_2$O 8:2) MS(FAB): 1281(M-H)$^-$, 1317(M+Cl)$^-$ trisacrylate: R$_f$ value: 0.60 (CH$_3$CN/H$_2$O 8:2) MS(FAB): 1463(M+Na)$^+$, 1475(M+Cl)$^-$ In addition to the above bis- and tris-acrylates it is also possible to detect analytically in the reaction solution higher-substituted derivatives, such as, for example:

tetrakisacrylate: 1616(M+Na)$^+$
pentakisacrylate: 1771(M+Na)$^+$
hexakisacrylate: 1926(M+Na)$^+$

EXAMPLE 12

Bis- and tris-O-[2(methacryloyloxy)ethyl-carbamoyl]-β-cyclodextrin 1.0 g (0.88 mmol) of β-CD are dissolved in 15 ml of pyridine and at 0° C. diluted dropwise with 2.74 g (1.8 mmol) of 2-isocyanatoethyl methacrylate (IEM). After 2 days 100 ml of toluene are added to the reaction mixture which is then concentrated completely in vacuo. The residue is chromatographed on silica gel with acetonitrile/water 8:2. Removal of the solvent yields the title compounds in amorphous form.

bisacrylate: R$_f$ value: 0.32(CH$_3$CN/H$_2$O 8:2) MS(FAB): 1445(M+H)$^+$, 1467(M+Na)$^+$ trisacrylate: R$_f$ value: 0.47 (CH$_3$CN/H$_2$O 8:2) MS(FAB): 1600(M+H)$^+$, 1622(M+Na)$^+$

EXAMPLE 13

Bis- and tris-O-[2(methacryloyloxy)ethyl-carbamoyl]-γ-cyclodextrin

Analogously to Example 11, the title compound is prepared from 20 g (15.4 mmol) of γ-CD and 7.2 g (46.3 mmol) of IEM in 250 ml of pyridine. A colourless powder is obtained.

bisacrylate: R$_f$ value: 0.52 (CH$_3$CN/H$_2$O 7:3) MS(FAB): 1629(M+Na)$^+$ trisacrylate: R$_f$ value: 0.66 (CH$_3$CN/H$_2$O 7:3) MS(FAB): 1762(M+H)$^+$, 1784(M+Na)$^+$

EXAMPLE 14

Bis- and tris-O-allylcarbamoyl-α-cyclodextrin

Analogously to Example 11, 20 g of α-cyclodextrin are reacted with 6.3 g (3.75 equivalents) of allyl isocyanate in pyridine. Colourless powders remain behind after purification.

bisallyl derivative: R$_f$ value: 0.30 (CH$_3$CN/H$_2$O 8:2) MS(FAB): 1139(M+H)$^+$, 1161(M+Na)$^+$ trisallyl derivative: R$_f$ value: 0.53 (CH$_3$CN/H$_2$O 8:2) MS(FAB): 1222(M+H)$^+$

EXAMPLE 15

Bis- and tris-O-[2(methacryloyloxy)ethyl-carbamoyl]-β-cyclodextrin 1.0 g (0.88 mmol) of β-CD are dissolved in 15 ml of pyridine and at 0° C. diluted dropwise with 2.74 g (1.8 mmol) of 2-isocyanatoethyl methacrylate (IEM). After 2 days 100 ml of toluene are added to the reaction mixture which is then concentrated completely in vacuo. The residue is chromatographed on silica gel with acetonitrile/water 8:2. Removal of the solvent yields the title compounds in amorphous form.

bisacrylate: R$_f$ value: 0.32 (CH$_3$CN/H$_2$O 8:2) MS(FAB): 1445(M+H)$^+$, 1467(M+Na)$^+$ trisacrylate: R$_f$ value: 0.47 (CH$_3$CN/H$_2$O 8:2) MS(FAB): 1600(M+H)$^+$, 1622(M+Na)$^+$

EXAMPLE 16

1-N-Ureido-1-deoxy-6-O-carbamoyl-bis(2-methylpropenoylethyl)-D-sorbitol 3.4 g of IEM are slowly added dropwise at room temperature to a solution of 2 g (11 mmol) of glucamine in 20 ml of dry pyridine. After being stirred for 1.5 hours the reaction solution is concentrated. The residue is then purified on 15 g of silica gel with ethyl acetate/methanol 8:2. The diacrylate is obtained in the form of a colourless solid.

C$_{20}$H$_{33}$N$_3$O$_{11}$(491.49) calc.: C(48.88%), H(6.77%), N(8.55%) found: C(48.32%), H(6.78%), N(8.51%).

EXAMPLE 17

Preparation of a Plasma-Modified Polymer Surface

A silicone film, which has been prepared by UV curing of Silicon PS 2067 (Hüls America Inc., Bristol, USA), is placed in a RF-GDP (radio frequency glow discharge plasma) reactor. The reactor is evacuated to 0.1 mbar. The silicone film is then exposed for 30 seconds to an oxygen plasma at 40 watts power and an oxygen gas flow rate of 10 cm$^3$/min. (STP). The reactor is then aerated.

EXAMPLE 18

Preparation of:

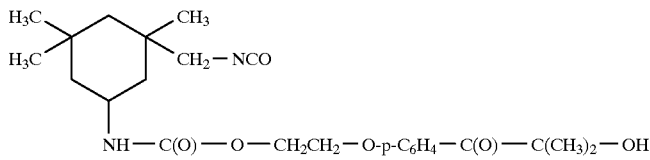

NH—C(O)—O—CH$_2$CH$_2$—O-p-C$_6$H$_4$—C(O)—C(CH$_3$)$_2$—OH

In a 500 ml flask equipped with a reflux condenser, a thermometer, a stirrer and a nitrogen inlet pipe, a solution of 11.125 g (0.05 mol) of freshly distilled isophorone diisocyanate (IPDI) in 50 ml of dry methylene chloride is mixed, under nitrogen, with a solution of 11.2 g (0.05 mol) of 4'-(β-hydroxyethoxy)-2-hydroxyprop-2-yl-phenone (Darocure 2959®) in 300 ml of dry methylene chloride; after the addition of 20 mg of dibutyltin dilaurate as catalyst, the mixture is stirred at room temperature for 48 hours. The progress of the reaction is followed by means of thin layer chromatography on silica gel plates (60 F$_{254}$, art. 5719 Merck) (eluant: toluene/acetonitrile 7:3). The resulting product is freed of small amounts of unreacted Darocure 2959 and bisadduct of IPDI by column chromatography on silica gel 60 (eluant: toluene/acetonitrile 7:3). Concentration of the pure fractions by evaporation on a rotary evaporator yields a colourless oil which crystallises slowly when cooled to −16° C. and is then recrystallised from dry diethyl ether. 15.6 g of a white crystalline product (70% of the theoretical yield) having a melting point of 76° C. are obtained.

The isocyanate content of the product is determined by titration with dibutylamine in toluene: calculated 2.242 mVal/g, found 2.25 mVal/g.

The method is described in "Analytical Chemistry of Polyurethanes" (High Polymer Series XVI/Part III, D. S. David+H. B. Staley, editors, Interscience Publishers, New York 1969 p. 86).

EXAMPLE 19

A silicone film prepared in accordance with Example 17 is dipped into an acetonitrile solution containing 1% of the photoinitiator from Example 18. As soon as the silicone film has been completely wetted it is removed from the said solution and then heated at 40° C. under dry nitrogen for 12 hours. After that time the silicone film is washed with acetonitrile (to remove excess photoinitiator) and then dried under a high vacuum at 0.001 mbar (0.1 Pa).

EXAMPLE 20

For comparison purposes, silicone films treated in accordance with Example 19 are sprayed on one side with HEMA (2 g in 6 ml of water) and on the other side with the bisadduct from Example 3 (1.02 g in 6 ml of water) so that a film of fluid approximately 10 μm thick is formed. The films that have been sprayed on both sides are irradiated, likewise on both sides, with a high pressure mercury lamp (Photoresistbelichter 82420, Oriel, 2000 W) under nitrogen for 3 minutes. The films so treated are then washed with water at room temperature for 24 hours. The contact angles in water are then measured.

|  | Dynamic contact angles in water | |
|---|---|---|
|  | Advancing Angle | Receding Angle |
| untreated film | 110° | 89° |
| HEMA-treated | 74° | 38° |
| treated with bisacrylate from Example 3 | 42° | 28° |

EXAMPLE 21

Analogously to Example 20, a lyophilised Ciba Vision STD soft lens (poly-HEMA) is coated with the bisacrylate from Example 3. Measurement of the contact angles gives the following values:

|  | Dynamic contact angles in water | |
|---|---|---|
|  | Advancing Angle | Receding Angle |
| Ciba Vision STD lens | 78° | 45° |
| treated with bisacrylate from Example 3 | 37° | 21° |

EXAMPLE 22

Analogously to Example 19, a silicone film (Silastic Film, Dow Corning Corp.) is modified first with oxygen plasma (analogously to Example 17) and then with the photoiniator from Example 18. Coating is then carried out analogously to Example 20 with the bis- and tris-acrylate mixture (1:1) from Example 3. Measurement of the contact angles gives the following values:

|  | Dynamic contact angles in water | |
|---|---|---|
|  | Advancing Angle | Receding Angle |
| untreated film | 115° | 88° |
| treated with mixture from Example 3 | 47° | 22° |

EXAMPLE 23

In a brown round-bottomed flask, 0.5 g of the bisacrylate from Example 3 and 4 mg of Darocure® 2959 photoinitiator (Ciba-Geigy) are dissolved in 1 ml of water. A suitable amount of that solution is introduced into small moulds with lens geometry and irradiated with a high pressure mercury lamp for 15 minutes. The blanks so obtained are extracted in water and their contact angles are then measured.

|  | Dynamic contact angles in water | |
| --- | --- | --- |
|  | Advancing Angle | Receding Angle |
| Lenses Example 23 | 35° | 30° |

EXAMPLE 24

Analogously to Example 23, the bis- and tris-acrylate mixture (1:1) from Example 3 is photopolymerised. The blanks are extracted in water and their contact angles are then measured.

|  | Dynamic contact angles in water | |
| --- | --- | --- |
|  | Advancing Angle | Receding Angle |
| Lenses Example 24 | 29° | 19° |

What is claimed is:

1. An ophthalmic lens comprising a polymer formed from a compound of formula I $$[R^1-(COO-Alk)_m-(OCONH-R)_n-NHCO-Y]_q-Z \quad (I)$$

wherein:
R$^1$ is a radically polymerizable hydrocarbon group;
m and n are each independently of the other 0 or 1;
q is an integer from 2 up to the fill valency of Z;
Alk is an alkylene having up to 10 carbon atoms;
R is a diradical, having up to 20 carbon atoms, of an organic diisocyanate;
each Y is independently —O— or —NH—; and
Z is a radical, less q hydroxy and optionally amino groups, of a saccharide selected from the group consisting of a mono-, di- or tri-saccharide, an oligosaccharide, a cyclodextrin (CD)$_2$ and an anhydrosaccharide;
with proviso that per saccharide unit Z, Y is —NH— a maximum of twice, and the remaining Y are —O—.

2. An ophthalmic lens according to claim 1 wherein q is from 2 to 5.

3. An ophthalmic lens according to claim 1 or 2 wherein per saccharide unit Z, Y is —NH— a maximum of once.

4. An ophthalmic lens according to claim 1 or 2 wherein Y is —O—.

5. An ophthalmic lens according to claim 1 wherein m is 1 and n is 0.

6. An ophthalmic lens according to claim 1 wherein m and n are 0.

7. An ophthalmic lens according to claim 1 wherein R1 is alkenyl, vinylphenyl or vinylbenzyl having up to 12 carbon atoms.

8. An ophthalmic lens according to claim 1 wherein Alk is a lower alkylene having up to 8 carbon atoms.

9. An ophthalmic lens according to claim 1 wherein the diradical R is lower alkylene, arylene, a saturated bivalent cycloaliphatic group having from 6 to 10 carbon atoms, alkylenearylene, arylenealkylene or arylenealkylenearylene.

10. An ophthalmic lens according to claim 1 wherein the radical Z is derived from a monosaccharide selected from the group consisting of an aldopentose, aldohexose, ketopentose and ketohexose.

11. An ophthalmic lens according to claim 1 wherein the radical Z is derived from a disaccharide selected from the group consisting of a trehalose, maltose, isomaltose, cellobiose, gentiobiose, saccharose, lactose, chitobiose, N,N-diacetylchitobiose, palatinose and sucrose.

12. An ophthalmic lens according to claim 1 wherein the radical Z is derived from a cyclodextrin.

13. An ophthalmic lens according to claim 1 wherein the radical Z is derived from an anhydrosaccharide.

14. An ophthalmic lens according to claim 1 wherein R$^1$ is alkenyl having from 2 to 8 carbon atoms; m is 1 and n is 0; q is from 2 to 4; Alk is lower alkylene having up to 4 carbon atoms; Y is —O—; and the radical Z is derived from a saccharide which is a 1-alkyl glycoside of an aldohexose, or a trehalose, a cyclodextrin or an anhydrosaccharide.

15. An ophthalmic lens according to claim 1 wherein R$^1$ is alkenyl having from 2 to 8 carbon atoms; m and n are 0; Y is —O— and —NH—; and the radical Z is derived from a saccharide which is a 1-alkyl glycoside of an aldohexose, or a trehalose, a cyclodextrin or an anhydrosaccharide.

16. An opthalmic lens according to claim 1 wherein R$^1$ is alkenyl having from 2 to 4 carbon atoms; m and n are 0; Y is —O—; and Alk is lower alkylene having up to 4 carbon atoms.

17. An opthalmic lens according to claim 1 wherein q is 2 and Z is a radical, less two hydroxy groups, of an anhydrosaccharide.

18. A process for the preparation of a compound of formula (I) as defined in claim 1, which process comprises reacting a saccharide of formula (II)

$$[Z]-X_q \quad (II),$$

wherein Z is as defined in claim 1 and X is a reactive group, for example a hydroxy or amino group, with q equivalents of a compound of formula (III)

$$R^1-(COO-Alk)_m-(OCONH-R)_n-NCO \quad (III)$$

wherein the variables are as defined in claim 1.

19. An ophthalmic lens comprising a polymerisation product of at least one compound of formula (I) as defined in claim 1 and of at least one further vinylic comonomer (a) that is different therefrom.

20. An ophthalmic lens according to claim 19 wherein the proportion by weight, based on the total polymer, of a compound of formula (I) is in the range of from 90 to 0.5%.

21. An opthalmic lens including a polymer according to claim 19 wherein the comonomer (a) is hydrophobic and is selected from the group consisting of C1–C18alkyl and C3–C18cycloalkyl acrylates and methacrylates, C3–C18 alkyl-acrylamides and -methacrylamides, acrylonitrile, methacrylonitrile, vinyl-C1–C18alkanoates, C2–C18alkenes, C2–C18 haloalkenes, styrene, lower alkylstyrenes, lower alkyl vinyl ethers, C2–C10perfluoroalkyl acrylates and methacrylates or correspondingly partially fluorinated acrylates and methacrylates, C3–C12perfluoroalkyl-ethyl-thiocarbonylaminoethyl acrylates and methacrylates, acryloxy- and methacryloxy-alkylsiloxanes, N-vinylcarbazole and C1–C12alkyl esters of maleic acid, fumaric acid, itaconic acid and mesaconic acid.

22. A polymer according to claim 19 wherein the comonomer (a) is hydrophilic and selected from the group consisting of hydroxy-substituted lower alkyl acrylates and methacrylates, acrylamide, methacrylamide, lower alkyl-acrylamides and -methacrylamides, ethoxylated acrylates and methacrylates, hydroxy-substituted lower alkyl-acrylamides and -methacryl amides, hydroxy-substituted lower alkyl vinyl ethers, sodium vinylsulfonate, sodium styrenesulfonate, 2-acrylamido-2-methylpropanesulfonic acid, N-vinylpyrrole, N-vinyl-2-pyrrolidone, 2- and 4-vinylpyridine, vinylically unsaturated carboxylic acids having a total of from 3 to 5 carbon atoms, amino-lower alkyl- (the term "amino" also including quaternary ammonium), mono-lower alkylamino-lower alkyl- and di-lower alkylamino-lower alkyl-acrylates and -methacrylates and allyl alcohol.

23. An ophthalmic lens according to claim 19 that is a contact lens.

24. A method of using as an article of manufacture having a surface coating which comprises a compound of formula (I):

$$[R^1-(COO-Alk)_m-(OCONH-R)_n-NHCO-Y]_q-Z \quad (I)$$

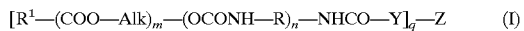

wherein:
$R^1$ is a radically polymerizable hydrocarbon group;
m and n are each independently of the other 0 or 1;
q is an integer from 2 up to the full valency of Z;
Alk is an alkylene having up to 10 carbon atoms;
R is a diradical, having up to 20 carbon atoms, of an organic diisocyanate;
each Y is independently —O— or —NH—; and
Z is a radical, less q hydroxy and optionally amino groups, of a saccharide selected from the group consisting of a mono-, di- or tri-saccharide, an oligosaccharide, a cyclodextrin (CD) and an anhydrosaccharide;
with proviso that per saccharide unit Z, Y is —NH— a maximum of twice, and the remaining Y are —O—.

25. A method of claim 24, wherein the article is a polymeric substrate.

26. A method of claim 25, wherein the article is a contact lens.

27. A method of using as a drug delivery system which comprises a polymer formed from at least one compound of formula (I):

$$[R^1-(COO-Alk)_m-(OCONH-R)_n-NHCO-Y]_q-Z \quad (I)$$

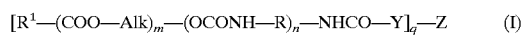

wherein:
$R^1$ is a radically polymerizable hydrocarbon group;
m and n are each independently of the other 0 or 1;
q is an integer from 2 up to the full valency of Z;
Alk is an alkylene having up to 10 carbon atoms;
R is a diradical, having up to 20 carbon atoms, of an organic diisocyanate;
each Y is independently —O— or —NH—; and
Z is a radical, less q hydroxy and optionally amino groups, of a saccharide selected from the group consisting of a mono-, di- or tri-saccharide, an oligosaccharide, a cyclodextrin (CD) and an anhydrosaccharide;
with proviso that per saccharide unit Z, Y is —NH— a maximum of twice, and the remaining Y are —O—.

* * * * *